United States Patent
Ishikawa et al.

(10) Patent No.: US 11,312,790 B2
(45) Date of Patent: *Apr. 26, 2022

(54) PRODUCTION METHOD FOR PENTOSAN POLYSULFATE

(71) Applicant: OJI HOLDINGS CORPORATION, Tokyo (JP)

(72) Inventors: Kotaro Ishikawa, Tokyo (JP); Takuro Kashiwamura, Tokyo (JP); Takuya Kato, Tokyo (JP); Toru Koga, Tokyo (JP); Suguru Ishikawa, Tokyo (JP)

(73) Assignee: OJI HOLDINGS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/643,265

(22) PCT Filed: Aug. 31, 2017

(86) PCT No.: PCT/JP2017/031434
§ 371 (c)(1),
(2) Date: Feb. 28, 2020

(87) PCT Pub. No.: WO2018/043668
PCT Pub. Date: Mar. 8, 2018

(65) Prior Publication Data
US 2020/0332027 A1 Oct. 22, 2020

(30) Foreign Application Priority Data

Aug. 31, 2016 (JP) .............................. JP2016-169710
Feb. 28, 2017 (JP) .............................. JP2017-035917

(51) Int. Cl.
*C08B 37/08* (2006.01)
*C08B 37/00* (2006.01)

(52) U.S. Cl.
CPC ........ *C08B 37/003* (2013.01); *C08B 37/0057* (2013.01)

(58) Field of Classification Search
None
See application file for complete search history.

(56) References Cited

U.S. PATENT DOCUMENTS

| 4,168,742 A | 9/1979 | Kluppel et al. |
| 4,699,900 A | 10/1987 | Bayol et al. |
| 4,713,373 A | 12/1987 | Bayol et al. |
| 4,727,063 A | 2/1988 | Naggi et al. |
| 5,516,765 A | 5/1996 | Andermann |
| 7,902,158 B2 | 3/2011 | Kuszmann et al. |
| 8,987,216 B2 | 3/2015 | Kuszmann et al. |
| 8,993,536 B2 | 3/2015 | Kakehi et al. |
| 2001/0005720 A1 | 6/2001 | Striker et al. |
| 2003/0109491 A1 | 6/2003 | Ulmer et al. |
| 2006/0194759 A1 | 8/2006 | Eidelson |
| 2007/0281893 A1 | 12/2007 | Kuszmann et al. |
| 2008/0249298 A1 | 10/2008 | Ulmer et al. |
| 2010/0055060 A1 | 3/2010 | Yoshida et al. |
| 2010/0261807 A1 | 10/2010 | Laine et al. |
| 2011/0118198 A1 | 5/2011 | Kuszmann et al. |
| 2011/0251154 A1 | 10/2011 | Stajic et al. |
| 2011/0281819 A1 | 11/2011 | Kakehi et al. |
| 2011/0306567 A1 | 12/2011 | Schofield et al. |
| 2016/0002365 A1* | 1/2016 | De Ferra ............. C08B 37/0057 536/119 |
| 2020/0062867 A1 | 2/2020 | Ishikawa et al. |

FOREIGN PATENT DOCUMENTS

| CA | 2018133 A1 | 12/1990 |
| CN | 1051564 A | 5/1991 |
| CN | 1832966 A | 9/2006 |
| CN | 101014607 A | 8/2007 |
| CN | 102061323 A | 5/2011 |
| CN | 102300870 A | 12/2011 |
| CN | 102766225 A | 11/2012 |
| CN | 103320548 A | 9/2013 |
| CN | 105907896 A | 8/2016 |
| CN | 106832020 A | 6/2017 |

(Continued)

OTHER PUBLICATIONS

Stephen Dealler et al., "Pentosan polysulfate as a prophylactic and therapeutic agent against prion disease", IDrugs, vol. 6, No. 5, Jun. 1, 2003, pp. 470-478, XP055777416 (10 pages total).

Extended European Search Report dated Feb. 26, 2021 from the European Patent Office in corresponding EP Application No. 17846672.8.

Extended European Search Report dated Feb. 3, 2021, from the European Patent Office in EP application No. 18809395.9, corresponding to U.S. Appl. No. 16/617,783.

"Technology of Wood Chemicals", CMC Publishing Co., Ltd., 2007, p. 108.

Koshijima, "Recent Problems of Hemicellulose Chemistry", Material, 1967, vol. 16, pp. 758-764.

(Continued)

*Primary Examiner* — Layla D Berry
(74) *Attorney, Agent, or Firm* — Sughrue Mion, PLLC

(57) ABSTRACT

The present invention provides a method for producing pentosan polysulfate, the method including a first step of obtaining an acidic xylooligosaccharide from a plant-derived raw material, and a second step of obtaining pentosan polysulfate from the acidic xylooligosaccharide. The first step includes a step of depolymerizing the plant-derived raw material. The second step includes a step of sulfating the acidic xylooligosaccharide. The method further includes a deacetylation step of adding a base to achieve a pH of 11 or higher. The deacetylation step is a step performed after the depolymerization step. The production method of the present invention can provide pentosan polysulfate having a low acetyl group content, and also produce pentosan polysulfate with a high yield inexpensively and efficiently.

17 Claims, 3 Drawing Sheets

(56) References Cited

FOREIGN PATENT DOCUMENTS

| | | |
|---|---|---|
| EP | 0 116 801 B1 | 4/1987 |
| ER | 0889055 A1 | 7/1999 |
| JP | S48-043100 B1 | 12/1973 |
| JP | S60-063203 A | 4/1985 |
| JP | S61-130301 A | 6/1986 |
| JP | S61-130302 A | 6/1986 |
| JP | S61-197601 A | 9/1986 |
| JP | S62-004362 B2 | 1/1987 |
| JP | H03-20225 A | 1/1991 |
| JP | H09-509650 A | 9/1997 |
| JP | H10-195107 A | 7/1998 |
| JP | H11-049802 A | 2/1999 |
| JP | H11-180821 A | 7/1999 |
| JP | 2003-183303 A | 7/2003 |
| JP | 2003-221307 A | 8/2003 |
| JP | 2003-221339 A | 8/2003 |
| JP | 2004-513185 A | 4/2004 |
| JP | 2005-501931 A | 1/2005 |
| JP | 2009-196915 A | 9/2009 |
| JP | 2009-532467 A | 9/2009 |
| JP | 2013-177433 A | 9/2013 |
| JP | 2014-129383 A | 7/2014 |
| JP | 2015-038061 A | 2/2015 |
| JP | 2016-514090 A | 5/2016 |
| JP | 6225321 B1 | 11/2017 |
| JP | 6281659 B1 | 2/2018 |
| WO | 1991/016058 A1 | 10/1991 |
| WO | 1995/014491 A3 | 6/1995 |
| WO | 1995/014492 A2 | 6/1995 |
| WO | 1998/006409 A2 | 2/1998 |
| WO | 02/041901 A1 | 5/2002 |
| WO | 2005/014656 A1 | 2/2005 |
| WO | 2005/117912 A1 | 12/2005 |
| WO | 2007/014155 A2 | 2/2007 |
| WO | 2007/123800 A2 | 11/2007 |
| WO | 2007/123800 A3 | 11/2007 |
| WO | 2007/138263 A1 | 12/2007 |
| WO | 2008/107906 A1 | 9/2008 |
| WO | 2009/087581 A1 | 7/2009 |
| WO | 2010/000013 A1 | 1/2010 |
| WO | 2010/089617 A2 | 8/2010 |
| WO | 2010/089617 A3 | 8/2010 |
| WO | 2012/101544 A1 | 8/2012 |
| WO | 2012/114349 A1 | 8/2012 |
| WO | 2013/186857 A1 | 12/2013 |
| WO | 2014/114723 A1 | 7/2014 |
| WO | 2014/122251 A2 | 8/2014 |
| WO | 2014/122251 A3 | 8/2014 |
| WO | 2016/184887 A1 | 11/2016 |
| WO | 2016/191698 A1 | 12/2016 |
| WO | 2018/043667 A1 | 3/2018 |
| WO | 2018/043668 A1 | 3/2018 |

OTHER PUBLICATIONS

International Preliminary Report on Patentability for PCT/JP2018/007138 dated Oct. 24, 2018 corresponding U.S. Appl. No. 16/489,074.
International Search Report for PCT/JP2018/007138 dated Mar. 27, 2018 corresponding to U.S. Appl. No. 16/489,074.
Ishihara et al., "Isolation of Xylan from Hardwood by Alkali Extraction and Steam Treatment", Mokuzai Gakkaishi, Journal of Wood Science 1996, vol. 42, No. 12, pp. 1211-1220 (11 pages total).
Kabel et al., "Hydrothermally treated xylan rich by-products yield different classes of xylo-oligosaccharides" Carbohydrate Polymers, 2002, vol. 50, No. 1, pp. 47-56.
Kabel et al., "Complex xylo-oligosaccharides identified from hydrothermally treated Eucalyptus wood and brewery's spent grain", Carbohydrate Polymers, 2002, vol. 50, No. 2, pp. 191-200.
Koutaniemi et al., "Distinct roles of carbohydrate esterase family CE16 acetyl esterases and polymer-acting acetyl xylan esterases in xylan deacetylation" Journal of Biotechnology, 2013, vol. 168, No. 4, pp. 684-692.
Pawar et al., "Acetylation of woody lignocellulose: significance and regulation" Frontiers in Plant Science, 2013, vol. 4, No. 118, pp. 1-8.
International Search Report for PCT/JP2017/031434 dated Oct. 31, 2017 corresponding to U.S. Appl. No. 16/643,265.
Office Action issued by the Japanese Patent Office dated Apr. 18, 2017 in JP Application No. 2017-040067.
Office Action issued by the Japanese Patent Office dated Oct. 3, 2017 in JP Application No. 2017-166559.
Moure et al., "Advances in the manufacture, purification and applications of xylo-oligosaccharides as food additives and nutraceuticals", Process Biochemistry, 2006, vol. 41, Issue 9, pp. 1913-1923.
Gullón et al., "Structural features and properties of soluble products derived from *Eucalyptus globulus* hemicelluloses" Food Chemistry, 2011, vol. 127, No. 4, pp. 1798-1807.
Gullón et al., "Membrane processing of liquors from *Eucalyptus globulus* autohydrolysis" Journal of Food Engineering, 2008, vol. 87, No. 2, pp. 257-265.
Ishikawa et al., "Research and development of sulphated hemicellulose (PPS)", The 62nd Japan Technical Association of the Pulp and Paper Industry Annual Meeting, 2019, pp. 1-5.
Scully et al., "The antiheparin effect of a heparinoid, pentosane polysulphate" Biochem. J, 1984, vol. 218, pp. 657-665.
McCarty et al., "Sulfated glycosaminoglycans and glucosamine may synergize in promoting synovial hyaluronic acid synthesis" Medical Hypotheses, 2000, vol. 54, No. 5, pp. 798-802.
Ferrao et al., "The effect of heparin on cell proliferation and type-I collagen synthesis by adult human dermal fibroblasts" Biochimica et Biophysica Acta, 1993, vol. 1180, pp. 225-230.
International Search Report for PCT/JP2018/020644 dated Sep. 4, 2018, corresponding to U.S. Appl. No. 16/617,783.
International Search Report for PCT/JP2017/031433 dated Oct. 31, 2017 corresponding to U.S. Appl. No. 16/643,215.
Office Action issued by the Japanese Patent Office dated Jan. 8, 2019 in JP Application No. 2018-553269.
Office Action issued by the Japanese Patent Office dated Feb. 5, 2019 in JP Application No. 2018-229611.
Hirst et al., "Water-soluble Polysaccharides of Cladophora" Journal of the Chemical Society, 1965, pp. 2958-2967.
International Search Report for PCT/JP2018/033535 dated Nov. 27, 2018.
International Search Report for PCT/JP2018/046537 dated Mar. 5, 2019.
International Search Report for PCT/JP2017/031432 dated Oct. 31, 2017.
Office Action issued by the Japanese Patent Office dated Jul. 17, 2019 in JP Application No. 2018-516078.
Office Action issued by the Japanese Patent Office dated Jul. 17, 2019 in JP Application No. 2018-516079.
González et al., "Demonstration of Inhibitory Effect of Oral Shark Cartilage on Basic Fibroblast Growth Factor-Induced Angiogenesis in the Rabbit Cornea" Biol. Pharm. Bull, 2001, vol. 24, No. 2, pp. 151-154.
Swain et al., "Heparin-Binding Growth Factor Blockade with Pentosan Polysulfate" Annals of the New York Academy of Sciences, 1993, vol. 698, pp. 63-70.
Zugmaier et al., "Polysulfated Heparinoids Selectively Inactivate Heparin-Binding Angiogenesis Factors" Annals of the New York Academy of Sciences, 1999, vol. 886, pp. 243-248.
Zugmaier et al., "Inhibition by Pentosan Polysulfate (PPS) of Heparin-Binding Growth Factors Released From Tumor Cells and Blockage by PPS of Tumor Growth in Animals" Journal of the National Cancer Institute, 1992, vol. 84, No. 22, pp. 1716-1724.
Garrote et al., "Non-isothermal autohydroiysis of *Eucalyptus wood*", Wood Science and Technology, 2002, vol. 36, pp. 111-123.
Sivová et al., "Fagus sylvatica glucuronoxylan sulfate-chemical profile and pharmacological view" Starch, 2015, vol. 68, pp. 621-628.
Rhee et al., "Engineering the Xylan Utilization System in Bacillus subtilis for Production of Acidic Xylooligosaccharides" Applied and Environmental Microbiology, 2014, vol. 80, No. 3, pp. 917-927.

(56) References Cited

OTHER PUBLICATIONS

Maekawa et al., "Infrared Spectra of Wood Cellulose and Related Polysaccharide" Kyoto University, Research Institute Report, 1968, vol. 43, pp. 1-8.
Kabel et al., "In Vitro Fermentability of Differently Substituted Xylo-oligosaccharides" Journal of Agricultural and Food Chemistry, 2002, vol. 50, pp. 6205-6210.
Office Action issued by Japanese Patent Office dated Oct. 9, 2018 in JP Application No. 2018-516078.
International Preliminary Report on Patentability dated Dec. 3, 2019 from the International Bureau in International Application No. PCT/JP2018/020644, corresponding to U.S. Appl. No. 16/617,783.
Office Action dated Nov. 16, 2020 in Australian Application No. 2018276567.
ELMIRON®-100 Mg (Pentosan Polysulfate Sodium)Capsules,2002, [https://www.accessdata.fda.gov/drugsatfda_docs/label/2020/020193s014lbl.pdf] (14 pages).
Office Action dated Mar. 25, 2021 issued by the Indian Patent Office in Indian Application No. 201947036653.
Office Action dated Apr. 27, 2021 in U.S. Appl. No. 16/646,243.
Office Action dated Mar. 2, 2021 in U.S. Appl. No. 16/489,074.
Stephan Daus et al., "Homogeneous Sulfation of Xylan from Different Sources", Macromolecular Materials and Engineering, 2011, vol. 296,pp. 551-561 (11 pages).
U.S. Appl. No. 16/617,783, filed Nov. 27, 2019, Kotaro Ishikawa et al.
U.S. Appl. No. 16/489,074, filed Aug. 27, 2019, Kotaro Ishikawa et al.
U.S. Appl. No. 16/643,215, filed Feb. 28, 2020, Kotaro Ishikawa et al.
U.S. Appl. No. 16/646,243, filed Mar. 11, 2020, Kotaro Ishikawa et al.
Teleman et al., "Characterization of O-acetyl-(4-O-methylglucurono)xylan isolated from birch and beech", Carbohydrate Research, 2002, vol. 337, pp. 373-377 (5 pages total).
Office Action dated Sep. 17, 2021 by Indian Patent Office in Indian Application No. 202047012044.
Office Action dated Aug. 30, 2021 by China National Intellectual Property Administration in Chinese Application No. 201780094371.2.
Mi et al., "Preparation of corn stover pentosan sulfate", Journal of Changchun University of Technology (Natural Science Edition), 2014, vol. 35, No. 6, pp. 716-719 (4 pages total).
Takayuki Ohbuchi et al., "Structural Analysis of Neutral and Acidic Xylooligosaccharides from Hardwood Kraft Pulp, and Their Utilization by Intestinal Bacteria in Vitro", Bioscience, Biotechnology, and Biochemistry, vol. 73, No. 9, 2009, pp. 2070-2076 (8 pages total).
Office Action dated Jun. 2, 2021 from the United States Patent and Trademark Office in U.S. Appl. No. 16/643,215.
Gura, "Cancer Models: Systems for Identifying New Drugs Are Often Faulty", Science, 1997, vol. 278, No. 5340, pp. 1041-1042 (6 pages total).
"The Merck Manual", Sixteenth Edition, 1992, pp. 339-342 and 1488-1490 (6 pages total).
Smith et al., "Cancer, inflammation and the AT1 and AT2 receptors", Journal of Inflammation, 2004, vol. 1, No. 3, pp. 1-12 (12 pages total).
Vergnolle et al., "Protease-activated receptors and inflammatory hyperalgesia", Mem Inst Oswaldo Cruz, Rio de Janeiro, 2005, vol. 100 (Suppl. I), pp. 173-176 (4 pages total).
Douglass et al., "1. Diagnosis, treatment and prevention of allergic disease: the basics", MJA Practice Essentials—Allergy, 2006, vol. 185, No. 4, pp. 228-233 (6 pages total).
Office Action dated Oct. 26, 2021 in U.S. Appl. No. 16/955,641.
Extended European Search Report dated Sep. 29, 2021 by European Patent Office in European Application No. 18890627.5.
Herbert et al., "Activity of Pentosan Polysulphate and Derived Compounds on Vascular Endothelial Cell Proliferation and Migration Induced by Acidic and Basic FGF In Vitro", Biochemical Pharmacology, 1988, vol. 37, No. 22, pp. 4281-4288 (8 pages total).
Office Action dated Oct. 25, 2021 issued by China National Intellectual Property Administration in Chinese Patent Application No. 201880058953.X, which corresponds to U.S. Appl. No. 16/646,243.
Communication dated Jan. 4, 2022 from the Indian Patent Office in Indian Application No. 202047029636, corresponding to U.S. Appl. No. 16/955,641.

* cited by examiner

PRODUCTION METHOD FOR PENTOSAN POLYSULFATE

CROSS REFERENCE TO RELATED APPLICATIONS

This application is a National Stage of International Application No. PCT/JP2017/031434 filed Aug. 31, 2017.

TECHNICAL FIELD

The present invention relates to a method for producing pentosan polysulfate.

BACKGROUND ART

Heparin has been used as a therapeutic agent for thrombosis, osteoarthritis, and the like. However, since heparin is a substance separated from the organs of animals, such as bovines or pigs, it is difficult to control the quality thereof. Further, there are cases where the use of heparin in treatment causes hesitation from the viewpoint of religious ethics etc. Therefore, the development of an alternative therapeutic agent that is free of animal-derived components, and that can be used instead of heparin, has been desired.

As such an alternative substance for heparin, pentosan polysulfate, for example, is known. Pentosan polysulfate is obtained by sulfating a plant-derived xylooligosaccharide. Since such pentosan polysulfate is a substance free of animal-derived components, its use as an alternative therapeutic agent for heparin has been expected (for example, Patent Literature (PTL) 1 and Patent Literature (PTL) 2).

PTL 1 and PTL 2 disclose a method for producing pentosan polysulfate, comprising sulfating xylan.

Xylans of hardwoods are known to have 5 to 7 acetyl groups per 10 xyloses at 2-position or 3-position under natural conditions (Non-patent Literature (NPL) 1). Patent Literature (PTL) 3 discloses that pentosan polysulfate for pharmaceutical use contains a xylose unit that binds to uronic acid at 4-position, and that is acetylated at 3-position.

CITATION LIST

Patent Literature

PTL 1: WO2010/000013
PTL 2: JPS48-043100A
PTL 3: WO2014/114723

Non-Patent Literature

NPL-1: CMC Publishing Co., Ltd., "*Wood Chemicals no Gijyutsu* (Techniques of Wood Chemicals)," First Edition 2007, p. 108

SUMMARY OF INVENTION

Technical Problem

An object of the present invention is to provide an inexpensive and efficient production method as a method for producing pentosan polysulfate.

Solution to Problem

As a result of intensive studies to solve the above problem, the present inventors have found that when a method for producing pentosan polysulfate includes a step of depolymerizing a plant-derived raw material and a sulfation step in this order, the efficiency of the method for producing pentosan polysulfate can be significantly improved. The inventors further found that when the method includes a deacetylation step after the depolymerization step, pentosan polysulfate can be produced with a higher yield than the yield achieved by a method that does not include a deacetylation step.

Specifically, the present invention has the following constitution.

[1] A method for producing pentosan polysulfate, comprising a first step of obtaining an acidic xylooligosaccharide from a plant-derived raw material; and a second step of obtaining pentosan polysulfate from the acidic xylooligosaccharide, the first step comprising a step of depolymerizing the plant-derived raw material, the second step comprising a step of sulfating the acidic xylooligosaccharide; and the method comprising a deacetylation step of adding a base to achieve a pH of 11 or higher, the deacetylation step being a step performed after the depolymerization step.

[2] The method for producing pentosan polysulfate according to [1], wherein the deacetylation step comprises stirring a solution containing the acidic xylooligosaccharide at a pH of 11 or higher for 1 hour or more.

[3] The method for producing pentosan polysulfate according to [1], wherein the deacetylation step comprises stirring a solution containing the acidic xylooligosaccharide at a pH of 12 or higher for 0.5 hours or more.

[4] The method for producing pentosan polysulfate according to any one of [1] to [3], wherein the base is sodium hydroxide.

[5] The method for producing pentosan polysulfate according to any one of [1] to [4], wherein the depolymerization step is performed under non-alkaline conditions.

[6] The method for producing pentosan polysulfate according to any one of [1] to [5], wherein the depolymerization step is a heat treatment step.

[7] The method for producing pentosan polysulfate according to [6], wherein the heat treatment step is a step of heating to 120° C. or higher under non-alkaline conditions.

[8] The method for producing pentosan polysulfate according to any one of [1] to [7], wherein the plant-derived raw material is a wood-derived raw material.

[9] The method for producing pentosan polysulfate according to any one of [1] to [8], further comprising a molecular weight adjustment step between the first step and the second step.

[10] The method for producing pentosan polysulfate according to [9], further comprising a post-molecular-weight-adjustment separation and purification step performed after the molecular weight adjustment step.

[11] The method for producing pentosan polysulfate according to any one of [1] to [10], wherein the second step further comprises a post-sulfation purification step performed after the sulfation step.

[12] The method for producing pentosan polysulfate according to [11], wherein the second step further comprises a powdering step performed after the post-sulfation purification step.

[13] A pentosan polysulfate produced by the method according to any one of [1] to [12].

[14] The pentosan polysulfate according to [13], which has an acetyl group content of 0 to 2.0 mass %.
[15] An anticoagulant comprising the pentosan polysulfate according to [13] or [14].

Advantageous Effects of Invention

The present invention provides a method for producing pentosan polysulfate having a low acetyl group content. The production method of the present invention can efficiently produce pentosan polysulfate with a high yield.

DESCRIPTION OF EMBODIMENTS

Figure 1:
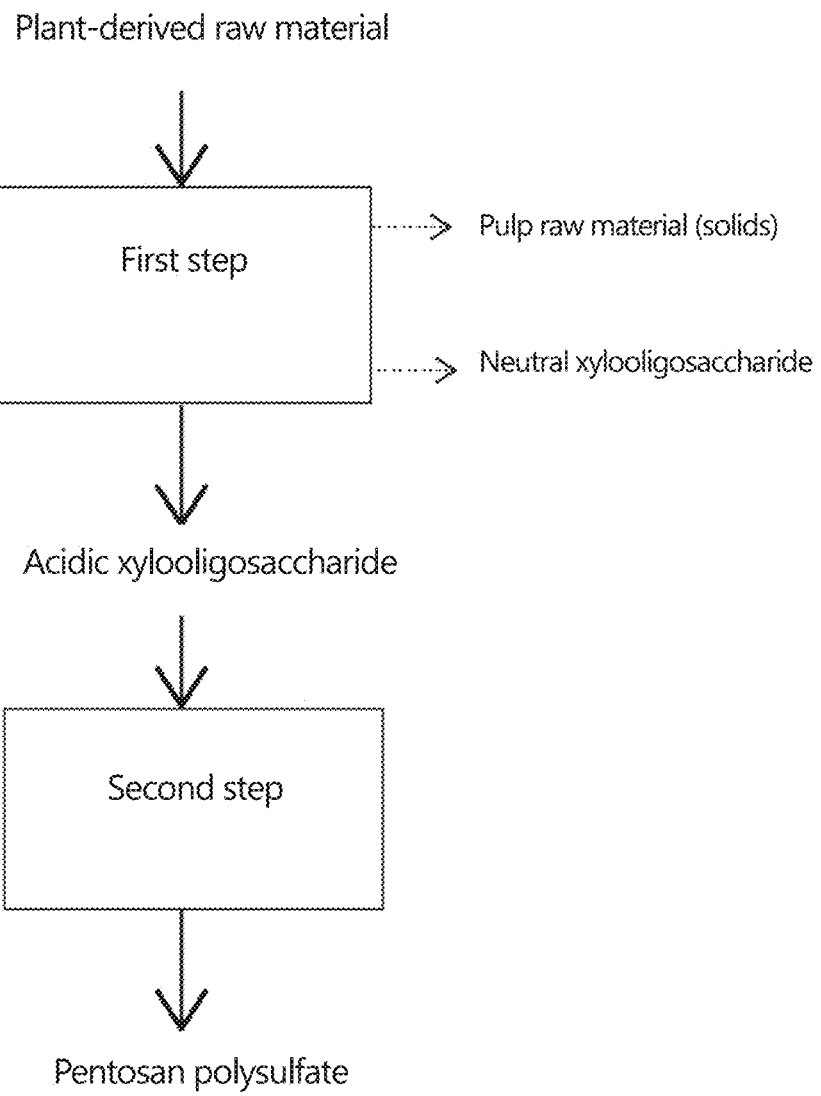
FIG. 1 is a diagram illustrating a process of producing pentosan polysulfate.

The present invention is described below in detail. The constituent features may be described below based on typical embodiments and specific examples; however, the present invention is not limited to these embodiments.
Method for Producing Pentosan Polysulfate
The present invention relates to a method for producing pentosan polysulfate derived from an acidic xylooligosaccharide.

The present invention relates to a method for producing pentosan polysulfate, which comprises a first step of obtaining an acidic xylooligosaccharide from a plant-derived raw material, and a second step of obtaining pentosan polysulfate from the acidic xylooligosaccharide, the method further comprising a deacetylation step. Since the production method of the present invention comprises a step of depolymerizing a plant-derived raw material and a sulfation step in this order, pentosan polysulfate can be efficiently produced. Since the production method of the present invention further comprises a deacetylation step, pentosan polysulfate can be produced with a high yield.

Pentosan polysulfate is a compound obtained by sulfating at least one hydroxyl group of xylooligosaccharide. The pentosan polysulfate as referred to herein includes salts of pentosan polysulfate, solvates of pentosan polysulfate, and solvates of salts of pentosan polysulfate. More specifically, the production method according to the present invention includes a method for producing a salt of pentosan polysulfate, a solvate of pentosan polysulfate, or a solvate of a salt of pentosan polysulfate. The salt of pentosan polysulfate is preferably a pharmaceutically acceptable salt. Examples include pentosan polysulfate sodium, pentosan polysulfate potassium, pentosan polysulfate calcium, and the like. The solvate is preferably a pharmaceutically acceptable solvate. Examples of solvents include water.

Pentosan polysulfate derived from an acidic xylooligosaccharide contains a structure represented by the following formula. The pentosan polysulfate may contain one structure represented by the following formula, or may contain two or more structures represented by the following formula. When the pentosan polysulfate contains two or more structures represented by the following formula, the following structure shows a repeating unit of pentosan polysulfate.

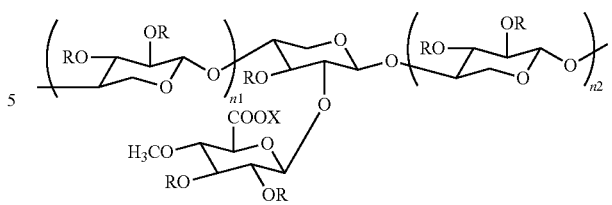

In the above formula, each R independently represents a hydrogen atom, —COCH$_3$, or —SO$_3$X$^1$; and at least one R is —SO$_3$X$^1$. X$^1$ is a hydrogen atom or a monovalent or divalent metal; preferably a hydrogen atom, sodium, potassium, or calcium; more preferably sodium, potassium, or calcium; and particularly preferably sodium. X represents a hydrogen atom or a monovalent or divalent metal; preferably sodium, potassium, or calcium; and particularly preferably sodium. n1 and n2 each independently represent an integer of 0 or more and 30 or less, and at least one of n1 and n2 is an integer of 1 or more.

In the above formula, n1+n2 is preferably 1 to 27, more preferably 2 to 18, and even more preferably 3 to 10.

In the above formula, X is preferably a monovalent or divalent metal, and is more preferably a pharmaceutically acceptable salt of pentosan polysulfate. For example, X is preferably sodium, potassium, or calcium. In such a case, the salt of pentosan polysulfate is pentosan polysulfate sodium, pentosan polysulfate potassium, or pentosan polysulfate calcium. Among these, it is particularly preferable that the salt of pentosan polysulfate is pentosan polysulfate sodium.

The pentosan polysulfate may contain one structure represented by the above formula, or may contain two or more structures represented by the above formula. When the pentosan polysulfate contains two or more structures represented by the above formula, the above structure shows a repeating unit of pentosan polysulfate.

The portion that is an end of the structure represented by the above formula and that does not bind to a structure represented by the above formula may be —OR. That is, —OR may bind to the left terminus (n1 side) of the above formula, whereas —R may bind to the right terminus (n2 side) of the above formula.

In the present invention, pentosan polysulfate can be obtained by sulfating an acidic xylooligosaccharide. The acidic xylooligosaccharide, which is one of the xylooligosaccharides, contains at least one uronic acid bound to at least one of the xylose units in a xylooligosaccharide molecule. That is, the acidic xylooligosaccharide has, as a side chain, at least one uronic acid residue per xylooligosaccharide molecule. The average number of uronic acid residues per molecule of acidic xylooligosaccharide is preferably 1 or more and 3 or less, more preferably 1 or more and 2 or less. The average number of uronic acid residues per molecule of acidic xylooligosaccharide can be measured by the carbazole-sulfuric acid method, or the colorimetric method using sodium tetraborate.

Based on the disclosure of WO2014/114723 and "*Wood Chemicals no Gijyutsu* (Techniques of Wood Chemicals)" (CMC Publishing Co., Ltd.) referred to above, it is assumed that known pentosan polysulfates include a certain amount of xylose units to which acetyl groups (—COCH$_3$), as well as uronic acid residue(s), bind. The pentosan polysulfate obtained by the production method of the present invention has a lower acetyl group content; in particular, the pentosan polysulfate has a lower content of acetyl groups binding to specific xylose units, as described above.

More specifically, the pentosan polysulfate obtained by the production method of the present invention has an acetyl group content of 0 to 2.0% by mass. The pentosan polysulfate preferably has an acetyl group content of 0 to 1.0 mass, more preferably 0 to 0.4 mass %, and even more preferably 0 to 0.3 mass %. It is particularly preferable that the acetyl group content of pentosan polysulfate is substantially 0 mass %. That is, it is particularly preferable that the pentosan polysulfate obtained by the production method of the present invention does not include pentosan polysulfate of the above formula wherein R is —$COCH_3$.

The acetyl group content of polysulfate pentosan can be calculated from the integral ratio of peaks in H-NMR measurement, as described in the Examples. More specifically, first, $^1$H-NMR measurement is performed using a H-NMR measurement solution containing a specific amount of pentosan polysulfate and a specific amount of an internal standard substance. By comparing the peak of a specific group of the internal standard substance and the peak of acetyl group in the obtained spectrum to obtain an integral ratio of the acetyl peak to the specific group, the molar amount of acetyl groups in the solution is obtained. The molar amount of acetyl groups is then multiplied by 43; and the obtained value is divided by the average molecular weight obtained separately, so as to obtain the mass % of acetyl groups.

Plant-Derived Raw Material

In the present invention, acidic xylooligosaccharide can be obtained by depolymerizing a plant-derived raw material. Examples of plant-derived raw materials include wood-derived raw materials, seed-derived raw materials, grain-derived raw materials, fruit-derived raw materials, and the like. Examples of plant-derived raw materials further include cottons such as cotton linter and cotton lint; herbaceous plants such as kenaf, hemp, ramie, and rice straw; and the like. Such raw materials derived from various sources may be used in combination as the plant-derived raw material.

Among these, wood-derived raw materials are particularly preferable as the plant-derived raw material. Examples of wood-derived raw materials include wood materials such as softwoods and hardwoods. The wood-derived raw material is preferably at least one selected from softwoods and hardwoods; and hardwoods are more preferable. The wood-derived raw material may be a mixture of softwood and hardwood. A bark may also be used as the wood-derived raw material.

Examples of hardwoods include beech, *Eucalyptus globulus*, *Eucalyptus grandis*, *Eucalyptus urograndis*, *Eucalyptus pellita*, *Eucalyptus braciana*, *Acacia mearnsii*, and the like. Examples of softwoods include Japanese cedar, Japanese cypress, pine, hiba, Japanese hemlock, and the like.

The wood-derived raw material preferably has a volume weight of 450 kg/m$^3$ or more and 700 kg/m$^3$ or less, and more preferably 500 kg/m$^3$ or more and 650 kg/m$^3$ or less. When the wood-derived raw material has a volume weight within the above-mentioned range, the efficiency of producing acidic xylooligosaccharide can be enhanced.

The wood-derived raw material is preferably wood chips obtained by crushing one or more of the above-mentioned woods. When wood chips are used as a plant-derived raw material, depolymerization of the plant-derived raw material can efficiently proceed, and the efficiency of producing acidic xylooligosaccharide can be enhanced.

First Step

Depolymerization Step

The method for producing pentosan polysulfate of the present invention comprises a first step of obtaining an acidic xylooligosaccharide from a plant-derived raw material, as shown in FIG. 1. In the method for producing pentosan polysulfate of the present invention, the first step comprises a step of depolymerizing a plant-derived raw material. In the step of depolymerizing a plant-derived raw material, the plant-derived raw material is chemically and/or physically decomposed to produce an acidic xylooligosaccharide. Examples of the chemical and/or physical decomposition step include a heat treatment step, an alkali treatment step, an acid treatment step, an enzyme treatment step, an ionic liquid treatment step, a catalytic treatment step, and the like. Among these steps, the depolymerization step is preferably at least one selected from a heat treatment step and an enzyme treatment step; and is more preferably a heat treatment step. The heat treatment step may be a heating and pressurizing step.

The depolymerization step is preferably performed under non-alkaline conditions (herein referred to as pH 9 or less, preferably pH 8 or less, and more preferably pH 7 or less).

The heat treatment step is a step of heating a plant-derived raw material in the presence of a solution. Since the plant-derived raw material is hydrolyzed in such a heat treatment step, the heat treatment step is sometimes referred to as a hydrolysis treatment step or a pre-hydrolysis treatment step. The solution used in the heat treatment step is preferably water. The ratio (mass ratio) of water to the plant-derived raw material is preferably in the range of 1:1 to 1:10. When the ratio of water to the plant-derived raw material is set within the above range, the hydrolysis reaction can proceed efficiently. The water used in the heat treatment step may be water added separately from the plant-derived raw material; or a part of the water used in the heat treatment step may be water originally contained in the plant-derived raw material.

In the heat treatment step, in addition to the plant-derived raw material and water, other chemicals may also be added. Examples of such other chemicals include alkalis, acids, and chelating agents. Chemicals that directly or indirectly assist the depolymerization of polysaccharides, such as scale inhibitors, pitch control agents, and ionic liquid, may also be added.

The heat treatment step is a step of heating a plant-derived raw material in the presence of water. The heating temperature (liquid temperature) in this step is preferably 30° C. or higher, more preferably 50° C. or higher, even more preferably 75° C. or higher, still even more preferably 90° C. or higher, particularly preferably 100° C. or higher, and most preferably 120° C. or higher. On the other hand, the heating temperature (liquid temperature) is preferably 300° C. or lower, more preferably 250° C. or lower, and even more preferably 200° C. or lower.

The treatment time in the heat treatment step can be determined, as appropriate, according to the treatment temperature. The treatment time is, for example, preferably 5 minutes or more, more preferably 10 minutes or more, and even more preferably 20 minutes or more. The P factor expressed by the following formula is a product of temperature and time in the heating treatment. It is preferable to adjust the P factor within a preferred range.

$$P = \int_{t_D}^{\tau} \frac{k_{H1(T)}}{k_{100° C.}} \cdot dt = \int_{t_0}^{\tau} \mathrm{Exp} \cdot \left(40.48 - \frac{15106}{T}\right) \cdot dt$$

In the above formula, P represents P factor, T represents absolute temperature (° C.+273.5), t represents heat treatment time, and $K_{H1(T)}/K_{100°C.}$ represents the relative rate of hydrolysis of glycosidic bonds.

In the heat treatment step, the P factor is preferably set at 200 or more, more preferably 250 or more, and even more preferably 300 or more. On the other hand, the P factor is preferably 1000 or less. In the heat treatment step, the P factor is adjusted as appropriate so that the average degree of polymerization of acidic xylooligosaccharide can be within a desired range, and the molecular weight of the obtained pentosan polysulfate can be thereby adjusted.

In the heat treatment step, the solution containing a plant-derived raw material preferably has a pH of 9 or less, more preferably a pH of 8 or less, and even more preferably a pH of 7 or less. That is, the heat treatment step is preferably performed under non-alkaline conditions. The pH value described above refers to the pH of the solution before the heat treatment.

In the heat treatment step, a raw material-derived acid may be dissociated, and acid hydrolysis may proceed at least partially. Examples of plant raw material-derived acids include organic acids, such as acetic acid and formic acid. In this case, the solution containing a plant-derived raw material has a further reduced pH after the acid hydrolysis.

The method for producing pentosan polysulfate preferably comprises a heat treatment step as the first step. This step can enhance the efficiency of producing acidic xylooligosaccharide, and thus lead to increased efficiency of producing pentosan polysulfate. When the method includes a heat treatment step as the first step, the production method can significantly reduce the number of steps required to produce acidic xylooligosaccharide, as compared with the conventional methods. When the method includes a heat treatment under non-alkaline conditions as the first step, the production method can efficiently produce acidic xylooligosaccharide with suppressed coloration because the acidic xylooligosaccharide is not substituted with hexenuronic acid.

In the present invention, the depolymerization step is preferably a heat treatment step; however, it may be a step other than the heat treatment step. For example, when the depolymerization step is an enzyme treatment step, the depolymerization step comprises a step of mixing a plant-derived raw material with an enzyme. Examples of usable enzymes include hemicellulase and the like. Specific examples include commercially available enzyme preparations, such as Cellulosin HC100 (trade name, manufactured by HBI Enzymes Inc.), Cellulosin TP25 (trade name, manufactured by HBI Enzymes Inc.), Cellulosin HC (trade name, manufactured by HBI Enzymes Inc.), Cartazyme (trade name, manufactured by Clariant AG), Ecopulp (trade name, manufactured by Rohm Enzyme GmbH), Sumizyme (trade name, manufactured by Shin Nihon Chemicals Corporation), Pulpzyme (manufactured by Novo Nordisk), and Multifect 720 (Genencor); and xylanase produced by microorganisms belonging to genus *Trichoderma*, genus *Thermomyces*, genus *Aureobasidium*, genus *Streptomyces*, genus *Aspergillus*, genus *Clostridium*, genus *Bacillus*, genus *Thermotoga*, genus *Thermoascus*, genus *Cardoceram*, genus *Thermomonospora*, or the like.

In the enzyme treatment step, an enzyme is added to a solution obtained by mixing a plant-derived raw material with water. The temperature of the solution during this addition is preferably 10° C. or higher and 90° C. or lower, and more preferably 30° C. or higher and 60° C. or lower. The temperature of the solution is preferably a temperature close to the optimal temperature of the enzyme used. The pH of the solution is also preferably adjusted to a range in which the activity of the enzyme is enhanced. For example, the pH of the solution is preferably adjusted to a pH of 3 or more and 10 or less.

When the depolymerization step is an alkali treatment step or an acid treatment step, the depolymerization step comprises a step of mixing a plant-derived raw material with an alkaline solution or an acid solution. In the alkali treatment step, sodium hydroxide or potassium hydroxide is preferably added. In the acid treatment step, hydrochloric acid, sulfuric acid, acetic acid, or the like is preferably added. In the above cases as well, heating or pressurization may be performed as appropriate.

When the depolymerization step is at least one selected from an enzyme treatment step, an alkali treatment step, and an acid treatment step, the production method may further comprise, after the treatment step, a squeezing step, an extraction step, a heating step, a filtration step, a separation step, a purification step, a concentration step, a desalting step, or the like. Further, the method may comprise a molecular weight reduction step after the treatment step. Examples of other steps include the steps described in JP2003-183303A, the contents of which are incorporated herein by reference.

Filtration Step

In the method for producing pentosan polysulfate of the present invention, the first step may further comprise a filtration step after the depolymerization step described above. In the filtration step, the reaction mixture is separated into solids of the plant-derived raw material, and a solution other than the solids. More specifically, when a filtration step is provided after the depolymerization step, the reaction product is separated into solids, which are used as a pulp raw material, and a filtrate. The solids used as a pulp raw material are subjected to a digestion step or the like as a post-step, to thereby provide a cellulose raw material (dissolving pulp).

The collected filtrate can be separated into a gas layer and a liquid layer. Since the gas layer contains a large amount of furfurals, these furfurals can be recovered from the gas layer to isolate furfurals. On the other hand, the liquid layer contains a large amount of hemicellulose including acidic xylooligosaccharide and neutral xylooligosaccharide. The acidic xylooligosaccharide contained in the liquid layer can be separated and purified in the step described below.

Separation and Purification Step

In the method for producing pentosan polysulfate, the first step may further comprise a separation and purification step that is performed after the depolymerization step. When the first step comprises the filtration step described above, a separation and purification step is preferably provided after the filtration step.

Figure 2:
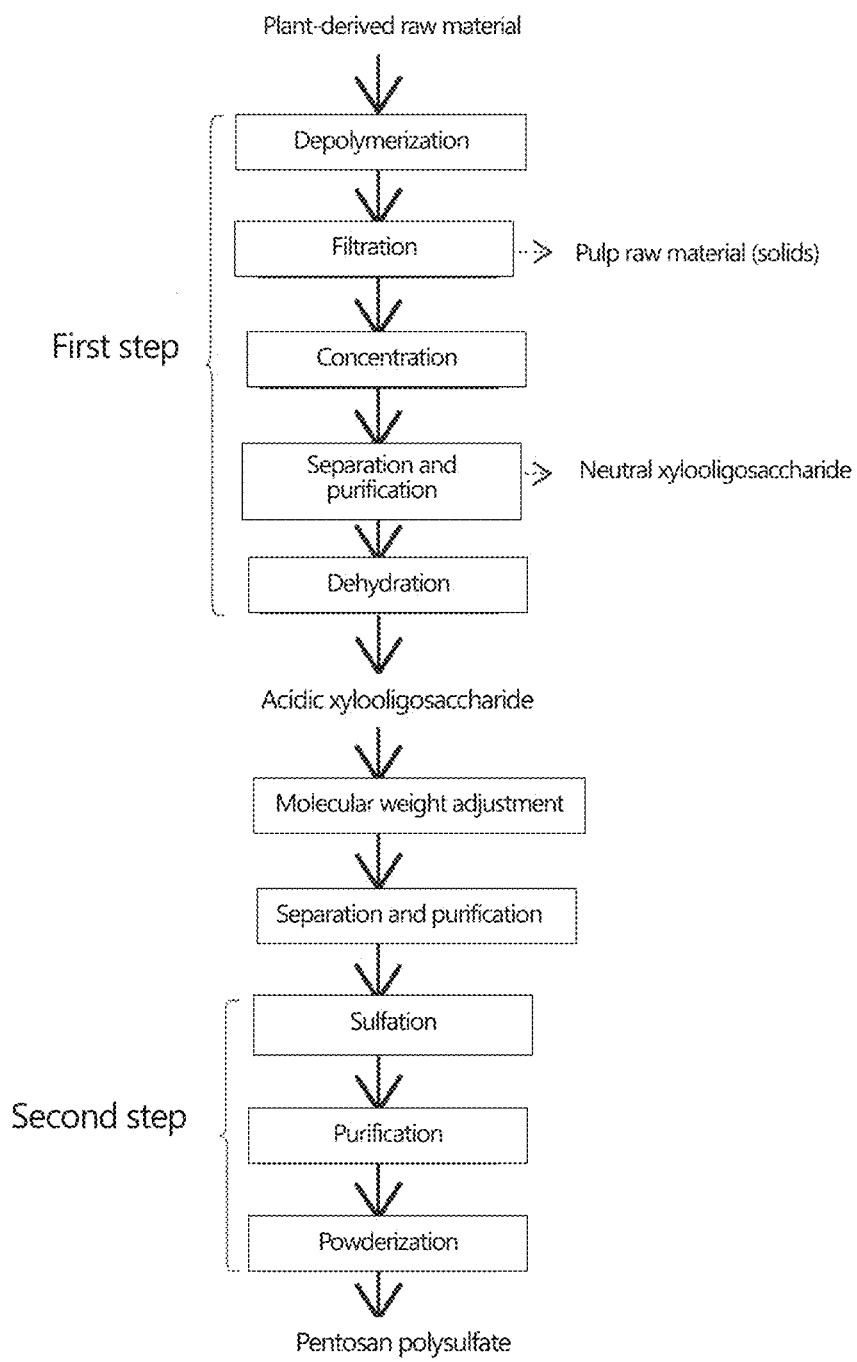
FIG. 2 is a diagram illustrating a process of producing pentosan polysulfate.

FIG. 2 shows a flow chart in which a filtration step is provided after the depolymerization step, and a separation and purification step is provided after the filtration step. The first step may include a separation and purification step performed immediately after the depolymerization step. Preferably, however, a filtration step is provided after the depolymerization step, and a step of separating acidic xylooligosaccharide from the obtained filtrate and purifying the acidic xylooligosaccharide is provided. The filtration step may be provided as a part of the separation and purification step; or may be provided as a step independent from the separation and purification step, as shown in FIG. 2. The separation and purification step is a step of separating and purifying acidic xylooligosaccharide. Since the filtrate obtained in the filtration step contains various saccharides, such as neutral xylooligosaccharide, in addition to acidic xylooligosaccharide, the separation and purification step is also a step of removing such xylooligosaccharides other than acidic xylooligosaccharide.

In the separation and purification step, for example, ion exchange chromatography, affinity chromatography, gel filtration, ion exchange treatment, NF membrane treatment, UF membrane treatment, RO membrane treatment, activated carbon treatment, or like methods are preferably used. In the separation and purification step, it is also preferable to perform the above methods in combination. In particular, when ion exchange chromatography is performed in the separation and purification step, acidic xylooligosaccharide can be selectively separated and purified. In ion exchange chromatography, acidic xylooligosaccharide is adsorbed to thereby mainly obtain acidic xylooligosaccharide from the sugar liquid (filtrate). Specifically, sugar liquid is first treated with a strong cation exchange resin to remove metal ions from the sugar liquid. Subsequently, using a strong anion exchange resin, sulfate ions or the like are removed from the sugar liquid. The resulting sugar liquid is treated with a weak anion exchange resin to adsorb acidic xylooligosaccharide on the resin. The acidic oligosaccharide adsorbed on the resin is eluted with a low-concentration salt (NaCl, $CaCl_2$, KCl, $MgCl_2$, etc.) to thereby obtain an acidic xylooligosaccharide solution containing a small amount of impurities.

Concentration Step

In the method for producing pentosan polysulfate of the present invention, the first step may further comprise a concentration step. The concentration step is preferably provided, for example, after the filtration step and before the separation and purification step, as shown in FIG. 2. When the first step includes a concentration step, the separation and purification step can be more efficiently performed, and the efficiency of producing pentosan polysulfate can be enhanced.

Examples of the concentration step include a membrane treatment step using an NF membrane, an ultrafiltration membrane, a reverse osmosis membrane, or the like; a concentration step using evaporation etc.; and the like.

In the concentration step, the solution is preferably concentrated, so that the resulting concentrate has an acidic xylooligosaccharide content of 10% or more and 80% or less, and more preferably 20% or more and 60% or less, based on the total mass of the concentrate.

Dehydration Step

In the first step, the acidic xylooligosaccharide may be obtained in the form of an acidic xylooligosaccharide solution; or may be subjected to a dehydration step, and obtained in the form of an acidic xylooligosaccharide concentrate or an acidic xylooligosaccharide powder. When acidic xylooligosaccharide powder is to be produced, the production method preferably further comprises a powdering step after the separation and purification step. In the present invention, when the method includes a dehydration step, sulfation in the sulfation step described below can proceed efficiently.

In the powdering step, the acidic xylooligosaccharide solution obtained in the separation and purification step is treated using, for example, a spray dryer, a freeze-drying machine, a hot-air drying machine, or a water-soluble organic solvent, to thereby obtain an acidic xylooligosaccharide powder.

Second Step
Sulfation Step

As shown in FIG. 1, the method for producing pentosan polysulfate of the present invention includes a first step and a second step, wherein the acidic xylooligosaccharide obtained in the first step is sulfated in the second step to thereby obtain pentosan polysulfate. That is, the second step includes a sulfation step.

The average degree of polymerization of acidic xylooligosaccharide to be subjected to sulfation is preferably adjusted, as appropriate, according to the molecular weight of pentosan polysulfate to be obtained as a final product.

The average degree of polymerization of acidic xylooligosaccharide can be calculated by dividing the total sugar amount of the acidic xylooligosaccharide by the amount of reducing sugar. In calculation of the total sugar amount, first, an acidic xylooligosaccharide solution is maintained at 50° C. and centrifuged at 15000 rpm for 15 minutes. The total sugar amount of the supernatant is then quantified by the phenol-sulfuric acid method ("*Kangento no Teiryo-Ho* (Method of Quantifying Reducing Sugar)"; published by Gakkai Shuppan Center). The calibration curve to be used in this quantification is produced using D-xylose (Wako Pure Chemical Industries, Ltd.). The amount of reducing sugar is quantified by the Somogyi-Nelson method ("*Kangento no Teiryo-Ho* (Method of Quantifying Reducing Sugar)"; published by Gakkai Shuppan Center). The calibration curve to be used in this quantification is also produced using D-xylose (Wako Pure Chemical Industries, Ltd.).

In the sulfation step, sulfuric acid or a sulfuric acid derivative is added to an acidic xylooligosaccharide solution to sulfate acidic xylooligosaccharide. Examples of sulfuric acid derivatives include sulfur trioxide pyridine complex, chlorosulfonic acid, and the like. In this step, the concentration of the acidic xylooligosaccharide solution is preferably 0.1 mass or more and 20 mass % or less. Sulfuric acid is preferably added to a concentration of 0.1 mass % or more and 50 mass- or less to the acidic xylooligosaccharide solution of the above-mentioned concentration. After the addition of sulfuric acid, the acidic xylooligosaccharide solution preferably has a pH of 1 or more and 9 or less.

Post-Sulfation Purification Step

In the method for producing pentosan polysulfate of the present invention, the second step may further comprise a post-sulfation purification step after the sulfation. When the method includes such a post-sulfation purification step, a high-purity pentosan polysulfate can be obtained.

In the post-sulfation purification step, a method such as centrifugation, membrane filtration, dialysis, water-soluble organic solvent treatment, or activated carbon treatment is preferably used. Among these, water-soluble organic solvent treatment and activated carbon treatment can selectively separate and purify sulfonated pentosan polysulfate, and are therefore preferably used.

Powdering Step

In the second step, sulfated pentosan polysulfate may be obtained in the form of a pentosan polysulfate solution; or may be subjected to a powdering step, and obtained in the form of a pentosan polysulfate powder. When pentosan polysulfate powder is to be produced, the production method preferably further comprises a powdering step after the post-sulfation purification step.

As the powdering step, for example, the pentosan polysulfate solution obtained in the post-sulfation purification step can be treated using a spray dryer, a freeze-drying machine, a hot-air drying machine, a water-soluble organic solvent, or the like, to thereby obtain a pentosan polysulfate powder.

Pentosan polysulfate is obtained by subjecting acidic xylooligosaccharide to the second step described above. The pentosan polysulfate thus obtained preferably has a sulfur content of 10 mass % or more and 20 mass % or less, based on the total mass of the pentosan polysulfate. The sulfur content of pentosan polysulfate can be determined by the oxygen flask combustion method described in General Tests of the Japanese Pharmacopoeia.

Deacetylation Step

The method for producing pentosan polysulfate of the present invention comprises a deacetylation step that is performed at any stage after the depolymerization step. The deacetylation step is a step for reducing the acetyl group content of pentosan polysulfate. More specifically, the deacetylation step is a step of adding a base to adjust the pH of a solution containing a substance obtained from a plant-derived raw material, such as acidic xylooligosaccharide (herein also referred to as a "solution containing acidic xylooligosaccharide or the like"), to pH 11 or more. In the deacetylation step, for example, the solution obtained after the depolymerization, the filtrate obtained by the filtration step, the solution containing acidic xylooligosaccharide after the separation and purification step and before the sulfation step, or the solution containing acidic xylooligosaccharide after the sulfation step (pentosan polysulfate) may be adjusted to a pH of 11 or higher. When the solution containing acidic xylooligosaccharide after the separation and purification step and before the sulfation step is adjusted to a pH of 11 or higher, a pentosan polysulfate of stable quality, having a reduced acetyl group content, can be obtained; and sites to which acetyl groups have been bonded can also be sulfated, thereby enhancing the sulfation efficiency and thus leading to increased efficiency of producing pentosan polysulfate. When the solution containing acidic xylooligosaccharide after the sulfation step (pentosan polysulfate) is adjusted to a pH of 11 or higher, the purification step can be performed more efficiently. The solution containing acidic xylooligosaccharide or the like is preferably an aqueous solution. The solution containing acidic xylooligosaccharide may herein also be referred to as the acidic xylooligosaccharide solution.

The pH in the deacetylation step is preferably pH 11 to 14, and more preferably pH 12 to 13. The solution subjected to the deacetylation step is preferably maintained at pH 11 or higher for 0.5 hours or more, more preferably at pH 11 or higher for 1.0 hour or more, even more preferably at pH 11 or higher for 2.0 hours or more, and particularly preferably at pH 11 or higher for 3.0 hours or more. In particular, when the pH is lower than 12, the solution is preferably maintained for 1.0 hour or more. Particularly preferred conditions can be, for example, conditions such that the solution is maintained at pH 12 to 13 for 3 hours or more.

While the solution is maintained in the pH range described above, the solution is preferably stirred. The temperature conditions while the solution is maintained in the pH range are not particularly limited; however, the temperature is preferably room temperature.

In the deacetylation step, at least a base is added to a solution to be subjected to the deacetylation step (e.g., a solution containing acidic xylooligosaccharide). As long as the desired pH can be achieved, the base to be added is not particularly limited, and is preferably sodium hydroxide.

The deacetylation step may comprise a pH adjustment step of adjusting, to less than pH 11, a solution having pH 11 or more due to a base added after the solution is maintained at the pH described above. In the pH adjustment step, the solution may be adjusted to, for example, pH 9 or less, pH 8 or less, pH 7 or less, pH 6 or less, pH 5 or less, pH 4 or less, or the like. The adjustment may be performed by adding an acid. Examples of acids include hydrochloric acid.

The deacetylation step may also preferably comprise a desalting step after the pH adjustment step. Desalting can be performed, for example, using a dialysis membrane or an NF membrane.

The deacetylation step may further comprise a step of powdering the obtained product for the subsequent treatment.

Other Steps

Molecular Weight Adjustment Step

The method for producing pentosane polysulfate may further comprise a molecular weight adjustment step between the first step and the second step. The molecular weight adjustment step may be performed either before or after the deacetylation step. FIG. 2 is a flow diagram including a molecular weight adjustment step between the first step and the second step. As shown in FIG. 2, in the molecular weight adjustment step, the molecular weight of the acidic xylooligosaccharide obtained in the first step is adjusted. For example, in the molecular weight adjustment step, the molecular weight of the acidic xylooligosaccharide can be reduced.

In the molecular weight adjustment step, a pentosan polysulfate having a weight average molecular weight of 1000 or more and 30000 or less can be obtained by performing a treatment such as acid treatment, alkali treatment, enzyme treatment, NF membrane treatment, UF membrane treatment, RO membrane treatment, gel filtration treatment, activated carbon treatment, ion exchange treatment, or electrodialysis treatment. In the molecular weight adjustment step, a membrane treatment or the like may be performed to selectively recover pentosan polysulfate having a desired weight average molecular weight.

Post-Molecular-Weight-Adjustment Separation and Purification Step

The method for producing pentosan polysulfate may further comprise a post-molecular-weight-adjustment separation and purification step performed after the molecular weight adjustment step. Examples of the post-molecular-weight-adjustment separation and purification step include gel filtration, ion exchange, NF membrane treatment, UF membrane treatment, RO membrane treatment, electrodialysis treatment, activated carbon treatment, water-soluble organic solvent treatment, chromatographic treatment, and the like. When the production method includes such a post-molecular-weight-adjustment separation and purification step, acidic xylooligosaccharide with a desired molecular weight obtained in the molecular weight adjustment step can be selectively recovered, and pentosan polysulfate having a narrow molecular weight distribution can be efficiently obtained.

The weight average molecular weight (Mw) of pentosan polysulfate obtained by the production method of the present invention is not particularly limited; and may be, for example, 5000 or less, 4000 or less, 3900 or less, 3800 or less, or 3750 or less. In this case, the lower limit of the weight average molecular weight (Mw) of the pentosan polysulfate is preferably 1000.

The weight average molecular weight (Mw) of pentosan polysulfate may be, for example, more than 5000, 6000 or more, 7000 or more, 10000 or more, 15000 or more, or 20000 or more.

The number average molecular weight (Mn) of pentosan polysulfate is not particularly limited; and may be, for example, 5000 or less, 4000 or less, 3900 or less, 3800 or less, or 3750 or less. In this case, the lower limit of the number average molecular weight (Mn) of pentosan polysulfate is preferably 300.

The number average molecular weight (Mn) of pentosan polysulfate may be more than 5000, may be 6000 or more, may be 7000 or more, may be 10000 or more, may be 15000 or more, or may be 20000 or more.

The weight average molecular weight (Mw) and the number average molecular weight (Mn) of pentosan polysulfate obtained by the production method of the present invention can be measured by GPC (gel permeation chromatography). As the GPC column, a YMC-Pack Diol-300 and YMC-Pack Diol-60 (both manufactured by YMC) connected to each other can be used. The GPC conditions can be, for example, the following conditions.
Eluent: 25 mM potassium dihydrogen phosphate/25 mM dipotassium hydrogen phosphate/50 mM potassium chloride
Flow rate: 0.7 mL/min
Measurement temperature: 40° C.
Detector: refractive index detector
Analysis time: 40 minutes The degree of dispersion of pentosan polysulfate obtained by the production method of the present invention is preferably 1.00 or more and 1.40 or less, more preferably 1.00 or more and 1.35 or less. The degree of dispersion of pentosan polysulfate is further preferably 1.00 or more and 1.20 or less. The degree of dispersion (D) of pentosan polysulfate is calculated by the following formula:

Degree of Dispersion(D)=Weight average molecular weight(Mw)/Number average molecular weight (Mn)

The pentosan polysulfate obtained by the production method of the present invention has high purity, and tends to have a narrow molecular weight distribution. The pentosan polysulfate obtained by the production method of the present invention has excellent quality stability.

Applications of Pentosan Polysulfate The pentosan polysulfate obtained by the production method of the present invention can be used for pharmaceuticals, foods, cosmetics, and like purposes. For example, a pharmaceutical composition containing, as an active ingredient, the pentosan polysulfate obtained by the production method of the present invention (pentosan polysulfate, pharmaceutically acceptable salt of pentosan polysulfate, or pharmaceutically acceptable solvates thereof) can be provided. In particular, since pentosan polysulfate has anticoagulant activity, the above pharmaceutical composition can be used as an anticoagulant.

In general, anticoagulant activity is based on the activity of inhibiting blood coagulation factors. That is, when anticoagulant activity is high, a blood coagulation reaction is inhibited. Blood coagulation factors refer to the action system of a series of molecules in a living body for coagulating blood when bleeding etc. Successive activation of a large number of blood coagulation factors agglutinates fibrin, and stops bleeding in the bleeding area. Representative examples of blood coagulation factors include factor Xa and factor IIa. Blood coagulation can be inhibited by inhibiting the activity of these factors.

The factor Xa inhibitory activity (anti-Xa activity) of pentosan polysulfate is preferably 0.10 IU/mg or more, and more preferably 0.12 IU/mg or more.

The factor IIa inhibitory activity (anti-IIa activity) of pentosan polysulfate is preferably 0.50 IU/mg or less, more preferably 0.40 IU/mg or less, and even more preferably 0.30 IU/mg or less.

Here, the factor Xa inhibitory activity (anti-Xa activity) can be measured using Test Team (registered trademark) Heparin S (manufactured by Sekisui Medical Co., Ltd.).

The factor IIa inhibitory activity (anti-IIa activity) can be measured using Biophen heparin anti-IIa (manufactured by Hyphen BioMed).

The activity ratio of the factor Xa inhibitory activity (anti-Xa activity) of pentosan polysulfate to the factor IIa inhibitory activity (anti-IIa activity) of pentosan polysulfate is preferably within a predetermined range. More specifically, the anti-Xa activity/anti-IIa activity ratio is preferably 0.50 or more, more preferably 1.00 or more, even more preferably 1.10 or more, and still even more preferably 1.20 or more.

The production method of the present invention can provide a pentosan polysulfate that has anti-Xa activity, anti-IIa activity, and anti-Xa activity/anti-IIa activity ratio controlled within the ranges described above. That is, a pentosan polysulfate that has anti-IIa activity lower than anti-Xa activity can be provided. When the anti-Xa activity/anti-IIa activity ratio is controlled to fall within the above-mentioned range, the anticoagulant activity can be more effectively increased; and the occurrence of side effects, such as an increased risk of bleeding or a decrease of platelets, can be suppressed.

Pharmaceutical compositions comprising pentosan polysulfate obtained by the production method of the present invention can be used, for example, as surface treatment agents for medical devices or medical materials. Such a pharmaceutical composition can be used, for example, as a surface treatment agent for implantable artificial organs, artificial blood vessels, catheters, stents, blood bags, contact lenses, intraocular lenses, and surgical auxiliary instruments. As a method for immobilizing the pharmaceutical composition on the surface of a medical device or a medical material, there is, for example, a method comprising allowing the pharmaceutical composition to be in contact with a medical device or a medical material, and irradiating the contact portion with a radiation beam.

Such pharmaceutical compositions can be used as oral agents or external preparations.

EXAMPLES

The features of the present invention are described below more specifically with reference to Production Examples. The materials, amounts used, proportions, treatment content, treatment procedures, and the like described in the following Production Examples can be appropriately changed as long as such changes do not depart from the spirit of the present invention. Accordingly, the scope of the present invention should not be construed as being limited by the following specific examples.

Example 1

Production of Acidic Xylooligosaccharide

Forty parts by mass of water was added to 10 parts by mass of wood chips (hardwood), and a heat treatment was performed at 160° C. for 3 hours. The resulting mixture was then subjected to solid-liquid separation using a Screw Press (manufactured by Shinryo Seisakusho: 250×1000 SPH-EN), and the filtrate was recovered. The filtrate was further filtered through a bag filter with a micron rate of 1 μm (manufactured by ISP Filters). After 5 parts by mass of activated carbon (PM-SX; manufactured by Mikura Kasei Kabushiki Kaisha) was added to treat the filtrate at 50° C. for 2 hours, the treatment mixture, including the activated carbon, was further filtered through a ceramic filter with a micron rate of 0.2 μm (manufactured by Nihon Pall Co., Ltd.) to recover a clear filtrate. After the clear filtrate was concentrated 20 times with a reverse osmosis membrane (NTR-7450; manufactured by Nitto Denko Corporation) to obtain a concentrated sugar liquid, the concentrated sugar liquid was passed at SV 1.5 through a 4-bed 4-tower type ion exchange resin system consisting of a strong cationic resin (PK-218; manufactured by Mitsubishi Chemical Corporation), a weak anionic resin (WA30; manufactured by Mitsubishi Chemical Corporation), a strong cationic resin (PK-218; manufactured by Mitsubishi Chemical Corporation), and a weak anionic resin (WA30; manufactured by Mitsubishi Chemical Corporation). Acidic xylooligosaccharide was adsorbed on the weak anionic resin of the second and fourth towers. A 50 mM sodium chloride aqueous solution was then passed through the second and fourth towers at SV 1.5 to recover an acidic xylooligosaccharide solution with an average polymerization degree of less than 8. Sodium hydroxide was added to the obtained acidic xylooligosaccharide solution to achieve the pH shown in the table, and the resulting mixture was stirred for the period of time shown in the table for deacetylation. Hydrochloric acid was added to the obtained solution to achieve a pH of less than 5, and desalting was performed using a dialysis membrane (Spectra/Por; manufactured by Spectrum). The obtained acidic xylooligosaccharide solution was powdered using a freeze-drying machine (manufactured by Eyela).

Production of Pentosan Polysulfate Sodium 10 mL of N,N-dimethylformamide, 2.4 g of sulfur trioxide pyridine complex, and 0.3 g of the acidic xylooligosaccharide powder produced by the above-described method were added to a 100 mL separable flask, and allowed to react at 40° C. for 3 hours. After cooling, the obtained reaction mixture was added dropwise to 500 mL of ethanol. The generated precipitate was collected by filtration, and 30 mL of water was added to dissolve the precipitate therein. A sodium hydroxide solution was added to this solution to achieve a pH of 10. The resulting solution was added dropwise to 500 mL of ethanol, and the obtained precipitate was collected by filtration. Thereafter, 50 mL of water was added to dissolve the precipitate therein. After activated carbon was added to the solution and stirred, the resulting mixture was filtered. The filtrate was concentrated using an evaporator, and powdered using a freeze-drying machine (manufactured by Eyela).

Acetyl Group Content 35 mg of sodium 3-(trimethylsilyl)propionate-2,2,3,3-d4 (Isotec Corporation) was dissolved in heavy water (Kanto Kagaku). Using a 25-mL measuring flask, the solution was diluted to prepare an internal standard solution. The pentosan polysulfate sodium obtained in each of the Examples and Comparative Examples was weighed (30 mg), and dissolved in 1 mL of the internal standard solution to prepare a solution for NMR analysis. The obtained solution was transferred to an NMR sample tube (Kanto Kagaku), and $^1$H-NMR measurement was performed using FT-NMR (JNM-LA400; JEOL Ltd.). The acetyl group content was calculated from the integral ratio of the acetyl peak of pentosan polysulfate sodium to the trimethylsilyl peak of the internal standard substance.

Weight Average Molecular Weight of Pentosan Polysulfate Sodium

The weight average molecular weight (Mw) of pentosan polysulfate sodium shown in Table 1 was measured by GPC (gel permeation chromatography). As the GPC column, a YMC-Pack Diol-300 and YMC-Pack Diol-60 (both manufactured by YMC) connected to each other were used. GPC was performed under the following conditions.

Eluent: 25 mM potassium dihydrogen phosphate/25 mM dipotassium hydrogen phosphate/50 mM potassium chloride Flow rate: 0.7 mL/min Measurement temperature: 40° C.

Detector: refractive index detector

Analysis time: 40 minutes

Sulfur Content

The sulfur content of pentosan polysulfate sodium was measured by the oxygen flask combustion method described in the Japanese Pharmacopoeia.

Measurement of Anti-Xa Activity

The anti-Xa activity of pentosan polysulfate sodium was measured using Test Team (registered trademark) Heparin S (manufactured by Sekisui Medical Co., Ltd.).

Measurement of Anti-IIa Activity

The anti-IIa activity of pentosan polysulfate sodium was measured using Biophen heparin anti-IIa (manufactured by Hyphen BioMed).

TABLE 1

|  | Comparative Example 1 | Example 1 | Example 2 | Example 3 | Example 4 | Example 5 |
|---|---|---|---|---|---|---|
| Deacetylation conditions | No treatment | pH 11 1 hr | pH 11 2 hr | pH 12 0.5 hr | pH 12 1 hr | pH 13 3 hr |
| Weight average molecular weight | 2211 | 2356 | 2325 | 2178 | 2129 | 2155 |
| Acetyl group content (Mass %) | 2.793 | 1.616 | 0.866 | 0.470 | 0.217 | 0.000 |
| Sulfur content (mass %) | 16.27 | 14.33 | 15.12 | 15.09 | 15.34 | 15.28 |
| Anti-IIa activity (IU/mg) | 0.0221 | 0.1405 | 0.1845 | 0.0676 | 0.0934 | 0.0976 |
| Anti-Xa activity (IU/mg) | 0.0840 | 0.2047 | 0.2588 | 0.2439 | 0.2419 | 0.2297 |
| Anti-Xa/anti-IIa activity ratio | 3.801 | 1.457 | 1.403 | 3.607 | 2.591 | 2.352 |

Figure 3:
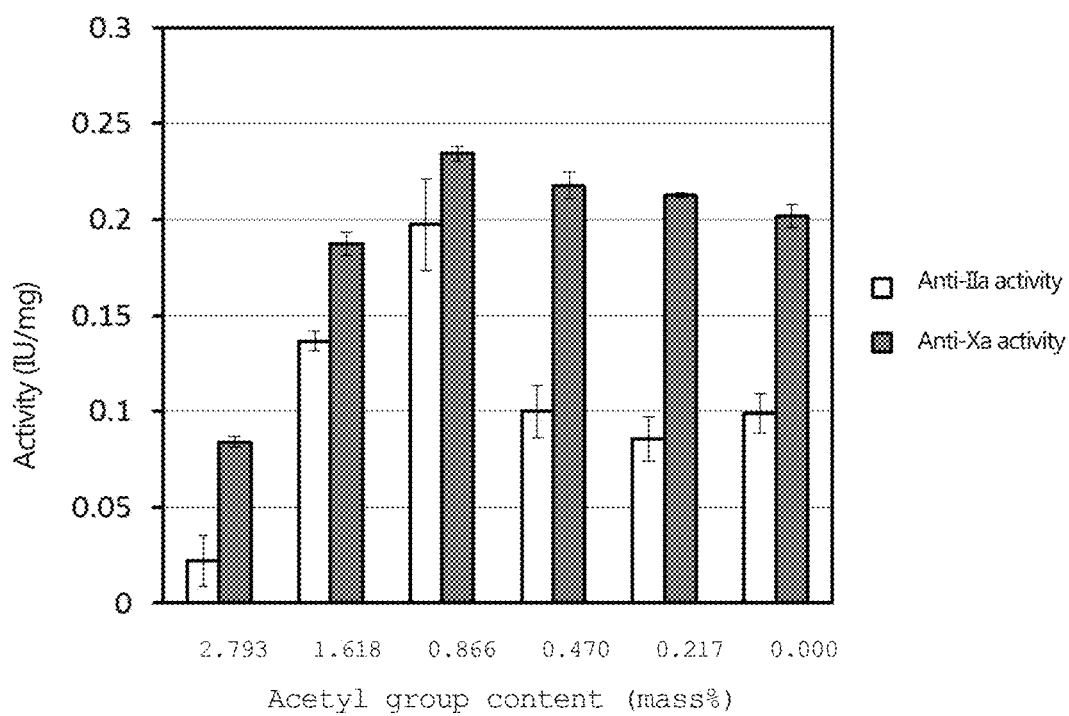
FIG. 3 is a graph showing anti-IIa activity and anti-Xa activity of pentosan polysulfates with different acetyl group contents obtained in the Examples and Comparative Examples.

The anti-IIa activity and anti-Xa activity in Table 1 are also shown in a graph (FIG. 3).

As can be seen from the results shown in Table 1 and FIG. 3, pentosan polysulfate sodium with a low acetyl group content obtained by any one of the production methods described in the Examples exhibits a preferable anti-Xa/anti-IIa activity ratio, and has anti-Xa activity higher than that of pentosan polysulfate sodium obtained by the production method described in the Comparative Example.

Table 2 shows the yield of pentosan polysulfate sodium when pentosan polysulfate sodium was obtained from acidic xylooligosaccharide powder under the conditions described in Comparative Example 1 or Example 5.

TABLE 2

| Comparative Example 1 | Example 5 |
|---|---|
| About 18.1% (yield: 0.1391 g, amount added: 0.3072 g) | About. 40.9% (yield: 0.3181 g, amount added: 0.3108 g) |

As can be seen from the results in Tables 1 and 2, when using the production method of the present invention, pentosan polysulfate sodium that exhibits a preferable anti-Xa/anti-IIa activity ratio, and that has sufficiently high anti-Xa activity, can be produced with a high yield.

The invention claimed is:

1. A method for producing pentosan polysulfate, comprising
   (i) depolymerizing a plant-derived raw material to obtain an acidic xylooligosaccharide from the plant-derived raw material,
   (ii) sulfating the acidic xylooligosaccharide to obtain pentosan polysulfate from the acidic xylooligosaccharide, and
   (iii) adding a base to achieve a pH of 12 or higher,
   wherein the step (iii) is performed after the step (i), and the method further comprises
   stirring a solution containing the acidic xylooligosaccharide at a pH of 12 or higher for 0.5 hours or more after adding the base.

2. The method for producing pentosan polysulfate according to claim 1, wherein the base is sodium hydroxide.

3. The method for producing pentosan polysulfate according to claim 1, wherein the step (i) is performed under non-alkaline conditions.

4. The method for producing pentosan polysulfate according to claim 1, wherein the step (i) is a heat treatment step.

5. The method for producing pentosan polysulfate according to claim 4, wherein the heat treatment step is a step of heating to 120° C. or higher under non-alkaline conditions.

6. The method for producing pentosan polysulfate according to claim 1, wherein the plant-derived raw material is a wood-derived raw material.

7. The method for producing pentosan polysulfate according to claim 1, further comprising a molecular weight adjustment step between the step (i) and the step (ii).

8. The method for producing pentosan polysulfate according to claim 7, further comprising a post-molecular-weight-adjustment separation and purification step performed after the molecular weight adjustment step.

9. The method for producing pentosan polysulfate according to claim 1, wherein the step (ii) further comprises a post-sulfation purification step performed after the sulfation step.

10. The method for producing pentosan polysulfate according to claim 9, wherein the step (ii) further comprises a powdering step performed after the post-sulfation purification step.

11. A method for producing pentosan polysulfate, comprising:
    (A) heating a wood-derived raw material to obtain an acidic xylooligosaccharide,
    (B) adding sulfuric acid or a sulfuric acid derivative to the acidic xylooligosaccharide, and
    (C) adding a base to a solution containing the acidic xylooligosaccharide to achieve a pH of 12 or higher,
    wherein the step (C) is performed after the step (A), and the method further comprises
    stirring a solution containing the acidic xylooligosaccharide at a pH of 12 or higher for 0.5 hours or more after adding the base.

12. The method for producing pentosan polysulfate according to claim 11, wherein the step (A) is performed under non-alkaline conditions.

13. The method for producing pentosan polysulfate according to claim 11, wherein the step (A) is a step of heating to 120° C. or higher under non-alkaline conditions.

14. The method for producing pentosan polysulfate according to claim 11, further comprising a molecular weight adjustment step between the step (A) and the step (B).

15. The method for producing pentosan polysulfate according to claim 14, further comprising a post-molecular-weight-adjustment separation and purification step performed after the molecular weight adjustment step.

16. The method for producing pentosan polysulfate according to claim 11, wherein the method further comprises a post-sulfation purification step performed after the step (B).

17. The method for producing pentosan polysulfate according to claim 16, wherein the method further comprises a powdering step performed after the post-sulfation purification step.

* * * * *

UNITED STATES PATENT AND TRADEMARK OFFICE
CERTIFICATE OF CORRECTION

| | |
|---|---|
| PATENT NO. | : 11,312,790 B2 |
| APPLICATION NO. | : 16/643265 |
| DATED | : April 26, 2022 |
| INVENTOR(S) | : Kotaro Ishikawa et al. |

Page 1 of 1

It is certified that error appears in the above-identified patent and that said Letters Patent is hereby corrected as shown below:

On the Title Page

Under item (30) Foreign Application Priority Data:
Delete "Aug. 31, 2016 (JP) ............ JP2016-169710
Feb. 28, 2017 (JP) ............ JP2017-035917", and
Insert --NONE-- therefor.

Signed and Sealed this
Second Day of August, 2022

Katherine Kelly Vidal
*Director of the United States Patent and Trademark Office*